(12) United States Patent
Mori et al.

(10) Patent No.: US 10,330,799 B2
(45) Date of Patent: Jun. 25, 2019

(54) X-RAY IMAGE PICKUP SYSTEM

(71) Applicant: Sharp Kabushiki Kaisha, Sakai, Osaka (JP)

(72) Inventors: Shigeyasu Mori, Sakai (JP); Kazuhide Tomiyasu, Sakai (JP)

(73) Assignee: SHARP KABUSHIKI KAISHA, Sakai (JP)

( * ) Notice: Subject to any disclaimer, the term of this patent is extended or adjusted under 35 U.S.C. 154(b) by 264 days.

(21) Appl. No.: 15/322,207

(22) PCT Filed: Jun. 25, 2015

(86) PCT No.: PCT/JP2015/068304
§ 371 (c)(1),
(2) Date: Dec. 27, 2016

(87) PCT Pub. No.: WO2016/002611
PCT Pub. Date: Jan. 7, 2016

(65) Prior Publication Data
US 2017/0139057 A1    May 18, 2017

(30) Foreign Application Priority Data
Jun. 30, 2014   (JP) ................................ 2014-134516

(51) Int. Cl.
*H04N 5/32* (2006.01)
*H01L 27/146* (2006.01)
(Continued)

(52) U.S. Cl.
CPC ........... *G01T 1/2018* (2013.01); *G01N 23/04* (2013.01); *G01T 1/20* (2013.01); *H01L 27/1225* (2013.01);
(Continued)

(58) Field of Classification Search
CPC ......... G01T 1/2018; G01T 1/20; G01N 23/04; G01N 2223/505; H01L 27/1225;
(Continued)

(56) References Cited

U.S. PATENT DOCUMENTS

| | | | |
|---|---|---|---|
| 6,034,725 | A | 3/2000 | Franklin et al. |
| 2012/0305777 | A1 | 12/2012 | Yamada et al. |

(Continued)

FOREIGN PATENT DOCUMENTS

| | | |
|---|---|---|
| JP | 10-511817 A | 11/1998 |
| JP | 2012-247327 A | 12/2012 |
| JP | 2013-175859 A | 9/2013 |

OTHER PUBLICATIONS

Official Communication issued in International Patent Application No. PCT/JP2015/068304, dated Sep. 1, 2015.

*Primary Examiner* — Courtney D Thomas
(74) *Attorney, Agent, or Firm* — Keating & Bennett, LLP (57) ABSTRACT

An X-ray image pickup system (10) includes an X-ray source (16), an image pickup panel (12), a scintillator (13), and an X-ray control unit (14E). The image pickup panel includes a photoelectric conversion element (26), a capacitor (50), a thin film transistor (24), and TFT control units (14A, 14B, 14F). To the photoelectric conversion element (26), scintillation light is projected. The capacitor (50) is connected to the photoelectric conversion element (26), and accumulates charges. The thin film transistor (24) is connected to the capacitor (50). The TFT control units (14A, 14B, 14F) control an operation of the thin film transistor (24). The thin film transistor (24) includes a semiconductor active layer (32) made of an oxide semiconductor. The X-ray control unit (14E) intermittently projects X-ray to the X-ray source (16). The TFT control units (14A, 14B, 14F) cause the thin film transistor (24) to operate when the X-ray is not (Continued)

projected, so as to read out the charges accumulated in the capacitor (50).

4 Claims, 6 Drawing Sheets

(51) Int. Cl.

| | |
|---|---|
| *G01T 1/20* | (2006.01) |
| *H01L 27/144* | (2006.01) |
| *G01N 23/04* | (2018.01) |
| *H01L 29/24* | (2006.01) |
| *H01L 29/786* | (2006.01) |
| *H01L 27/12* | (2006.01) |

(52) U.S. Cl.
CPC ......... *H01L 27/144* (2013.01); *H01L 27/146* (2013.01); *H01L 27/14605* (2013.01); *H01L 27/14609* (2013.01); *H01L 27/14612* (2013.01); *H01L 27/14663* (2013.01); *H01L 29/24* (2013.01); *H01L 29/7869* (2013.01); *H04N 5/32* (2013.01); *G01N 2223/505* (2013.01)

(58) Field of Classification Search
CPC .................. H01L 27/144; H01L 27/146; H01L 27/14609; H01L 27/14605; H01L 27/14612; H01L 27/14663; H01L 29/24; H01L 29/7869; H04N 5/32
USPC .................................................. 378/62, 98.8
See application file for complete search history.

(56) References Cited

U.S. PATENT DOCUMENTS

| | | |
|---|---|---|
| 2013/0222660 A1 | 8/2013 | Senda et al. |
| 2014/0072103 A1* | 3/2014 | Kitano ................ A61B 6/4233 378/62 |

* cited by examiner

<A-A cross section>

X-RAY IMAGE PICKUP SYSTEM

TECHNICAL FIELD

The present invention relates to an X-ray image pickup system, and more specifically, relates to an X-ray image pickup system that includes an image pickup panel that generates an image based on scintillation light obtained from X-ray that has passed through an object.

BACKGROUND ART

An X-ray image pickup system that picks up an image with use of an image pickup panel that includes a plurality of pixel portions is known. Among X-ray image pickup systems, there are those of a direct conversion type and those of an indirect conversion type.

An X-ray image pickup system of the direct conversion type, for example, converts projected X-ray into charges with use of an X-ray conversion film made of amorphous selenium (a-Se). The converted charges are accumulated in capacitors included in pixel portions. The accumulated charges are read out by causing thin film transistors included in the pixel portions to operate. Based on the charges thus read out, image signals are generated. Based on the image signals, an image is generated.

An X-ray image pickup system of the indirect conversion type, for example, converts projected X-ray into scintillation light by a scintillator. The scintillation light is converted into charges by photoelectric conversion elements included in pixel portions. The charges thus converted are read out by causing thin film transistors included in the pixel portions to operate. Based on the charges thus read out, image signals are generated. Based on the image signals, an image is generated.

DISCLOSURE OF THE INVENTION

An object of the present invention is to obtain a target image, while intermittently projecting X-ray, in an X-ray image pickup system of the indirect conversion type.

An X-ray image pickup system according to an embodiment of the present invention includes an X-ray source, an image pickup panel, a scintillator, and an X-ray control unit. The scintillator is arranged between the X-ray source and the image pickup panel, and converts X-ray projected from the X-ray source into scintillation light. The X-ray control unit controls an operation of the X-ray source. The image pickup panel includes a photoelectric conversion element, a capacitor, a thin film transistor, and a TFT control unit. To the photoelectric conversion element, the scintillation light is projected. The capacitor is connected to the photoelectric conversion element, and accumulates charges. The thin film transistor is connected to the capacitor. The TFT control unit controls an operation of the thin film transistor. The thin film transistor includes a semiconductor active layer. The semiconductor active layer is made of an oxide semiconductor. The X-ray control unit causes the X-ray source to project the X-ray intermittently. The TFT control unit causes the thin film transistor to operate when the X-ray is not projected, so as to read out the charges accumulated in the capacitor.

In an X-ray image pickup system according to an embodiment of the present invention, a target image can be obtained while X-ray is being intermittently projected.

MODE FOR CARRYING OUT THE INVENTION

An X-ray image pickup system according to an embodiment of the present invention includes an X-ray source, an image pickup panel, a scintillator, and an X-ray control unit. The scintillator is arranged between the X-ray source and the image pickup panel, and converts X-ray projected from the X-ray source into scintillation light. The X-ray control unit controls an operation of the X-ray source. The image pickup panel includes a photoelectric conversion element, a capacitor, a thin film transistor, and a TFT control unit. To the photoelectric conversion element, the scintillation light is projected. The capacitor is connected to the photoelectric conversion element, and accumulates charges. The thin film transistor is connected to the capacitor. The TFT control unit controls an operation of the thin film transistor. The thin film transistor includes a semiconductor active layer. The semiconductor active layer is made of an oxide semiconductor. The X-ray control unit causes the X-ray source to project the X-ray intermittently. The TFT control unit causes the thin film transistor to operate when the X-ray is not projected, so as to read out the charges accumulated in the capacitor.

In the above-described X-ray image pickup system, the semiconductor active layer is made of an oxide semiconductor. The off-current (leakage current) of the thin film transistor, therefore, is small. As a result, charges in an amount that approximately corresponds to projected scintillation light can be accumulated in the capacitor. Accordingly, even if an image is generated based on charges accumulated in the capacitor, a target image can be obtained.

The capacitor may be connected in parallel with respect to the photoelectric conversion element, or may be connected in series with respect to the photoelectric conversion element. In a case where the capacitor is connected in series, the capacitor is connected to the drain electrode of the thin film transistor.

Since the semiconductor active layer is made of an oxide semiconductor, a high-definition image can be obtained. The reasons for this are as follows.

In a thin film transistor in which a semiconductor active layer is made of an oxide semiconductor, the on-current thereof is approximately 20 times greater as compared with a conventional thin film transistor, and the off-current (leakage current) thereof is several orders of magnitude smaller as compared with a conventional thin film transistor. Since the on-current is greater, the size of the thin film transistor can be decreased. Since the off-current is smaller, the area of the accumulation capacitor can be decreased. Consequently, the pixel pitch can be decreased, which enables the image definition enhancement.

The oxide semiconductor is, for example, an oxide that contains indium (In), gallium (Ga), and zinc (Zn) at a predetermined ratio.

The thin film transistor further includes a gate electrode, a first insulating film, and a second insulating film. The first insulating film is formed between the gate electrode and the semiconductor active layer, and covers the gate electrode. The second insulating film covers the semiconductor active layer. Preferably, each of the first insulating film and the second insulating film includes a silicon oxide film. The silicon oxide film is formed in contact with the semiconductor active layer.

A silicon oxide film contains less hydrogen as compared with a silicon nitride film. It is therefore possible to suppress adverse influences that hydrogen contained in the semiconductor active layer, when being reduced, exerts to the properties of the thin film transistor.

The following describes more specific embodiments of the present invention, while referring to the drawings. Identical or equivalent parts in the drawings are denoted by the same reference numerals, and the descriptions of the same are not repeated.

Embodiment 1

Figure 1:
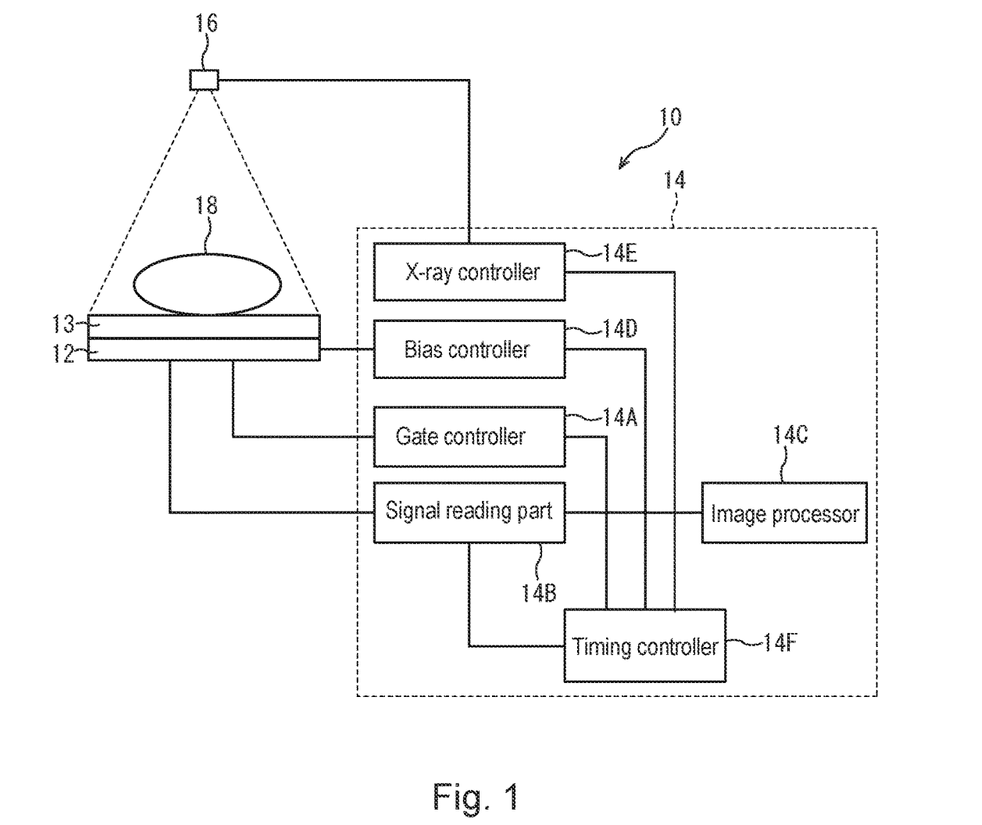
FIG. 1 is a schematic diagram illustrating a schematic configuration of an X-ray image pickup system according to Embodiment 1 of the present invention.

FIG. 1 illustrates an X-ray image pickup system 10 according to Embodiment 1 of the present invention. The X-ray image pickup system 10 includes an image pickup panel 12, a scintillator 13, a control unit 14, and an X-ray source 16.

In the X-ray image pickup system 10, X-ray that has been projected from the X-ray source 16 and passed through an object 18 is incident on the scintillator 13. The scintillator 13, when the X-ray is projected thereon, generates fluorescence (scintillation light). The scintillation light is picked up with the image pickup panel 12 and the control unit 14, whereby an image is acquired.

Figure 2A:
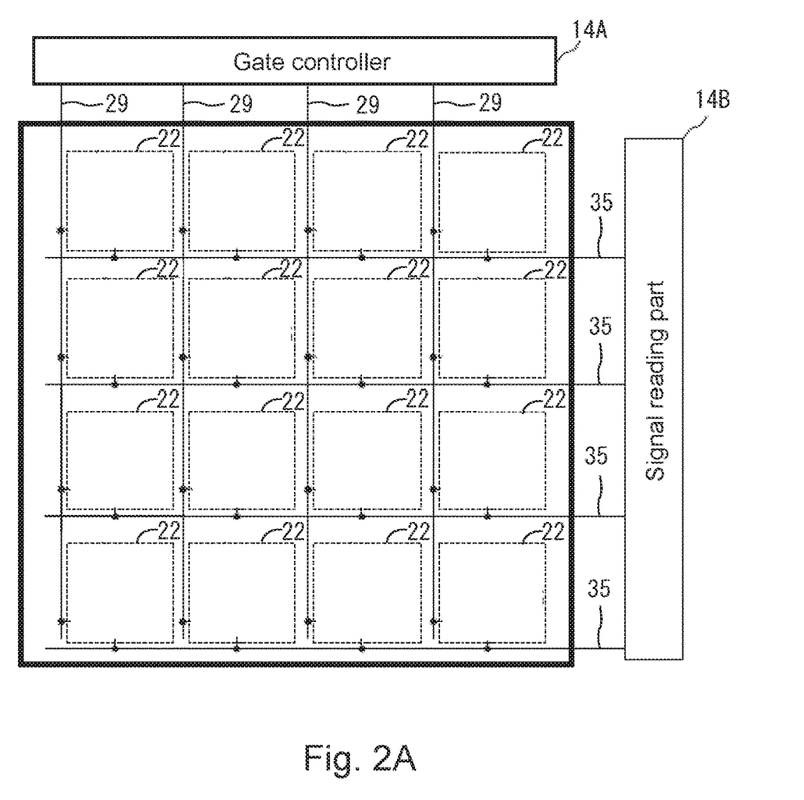
FIG. 2 is a schematic diagram illustrating an arrangement of a plurality of pixel portions included in an image pickup panel.

As illustrated in FIG. 2A, the image pickup panel 12 includes a plurality of pixel portions 22. The pixel portions 22 are arranged in a matrix, as illustrated in FIG. 2A. In the example illustrated in FIG. 2A, sixteen pixel portions 22 are arranged in matrix of four rows and four columns. The pixel portion 22 outputs a signal according to an intensity of scintillation light projected thereto (light detection signal).

Figure 3:
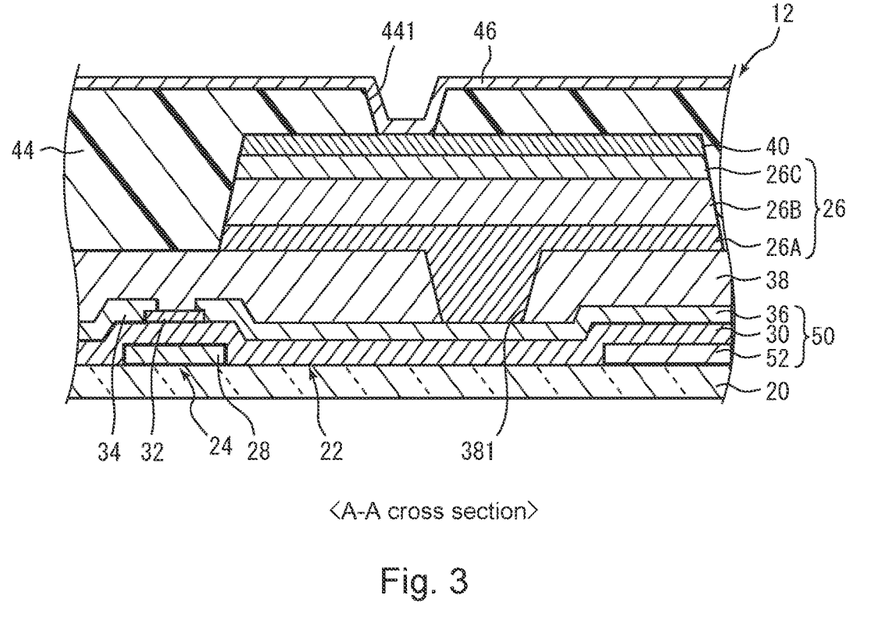
FIG. 3 is a cross-sectional view illustrating a schematic configuration of the pixel portion, taken along a line A-A in FIG. 4.

FIG. 3 is a cross-sectional view illustrating a schematic configuration of the pixel portion 22 included in the image pickup panel 12. The pixel portion 22 is formed on a substrate 20 included in the image pickup panel 12. The substrate 20 is not limited particularly and may be anything as long as it is an insulating substrate. The substrate 20 may be, for example, a substrate made of glass, or a substrate made of a synthetic resin. Examples of the synthetic resin include polyethylene terephthalate (PET), polyethylene naphthalate (PEN), polyether sulfone (PES), acryl, and polyimide.

Figure 2B:
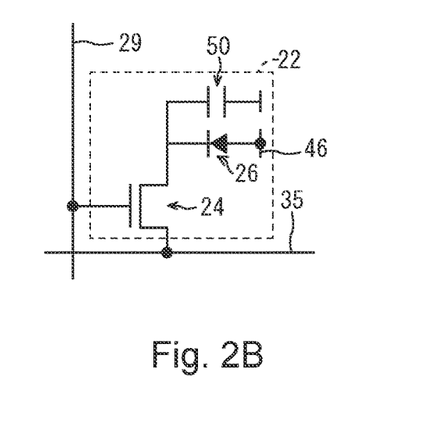
FIG. 2B illustrates an equivalent circuit of the pixel portion.

The pixel portion 22 includes a thin film transistor 24, a photodiode 26 as a photoelectric conversion element, and a capacitor 50, as illustrated in FIG. 2B. The capacitor 50 is connected in parallel with respect to the photodiode 26.

The thin film transistor 24 includes a gate electrode 28, a gate insulating film 30, a semiconductor active layer 32, a source electrode 34, and a drain electrode 36, as illustrated in FIG. 3.

Figure 4:
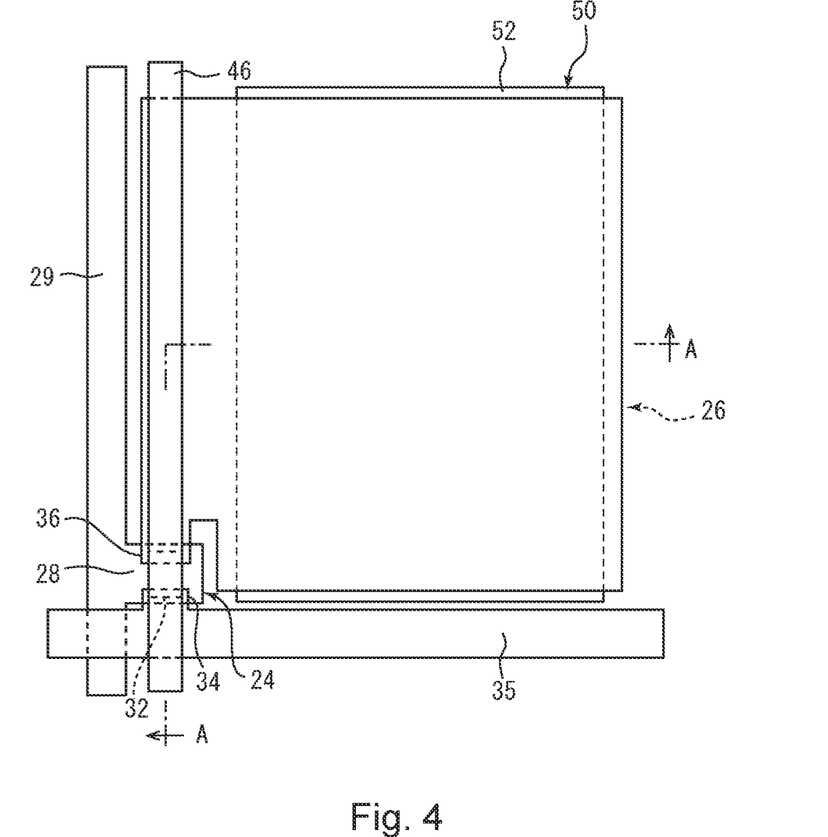
FIG. 4 is a plan view illustrating a schematic configuration of the pixel portion.

The gate electrode 28 is formed in contact with one of surfaces of the substrate 20, the surface being on one side in the thickness direction (hereinafter referred to as a principal surface), as illustrated in FIG. 3. The gate electrode 28 is made of, for example, a metal such as aluminum (Al), tungsten (W), molybdenum (Mo), tantalum (Ta), chromium (Cr), titanium (Ti), or copper (Cu), or an alloy of any of these, or alternatively, a nitride of the foregoing metal. The gate electrode 28 may be, for example, a laminate of a plurality of metal films. In the present embodiment, the gate electrode 28 has a laminate structure obtained by laminating a metal film made of titanium, a metal film made of aluminum, and a metal film made of titanium in the stated order. The gate electrode 28 is formed by, for example, forming a metal film on the substrate 20 by sputtering or the like, and patterning the metal film by photolithography. The gate electrode 28 has a thickness of, for example, 50 to 300 nm. The gate electrode 28 may be formed with a gate line that is formed on the substrate 20 and extends in a predetermined direction, or alternatively, formed with a part that extends from the gate line in a direction different from the foregoing predetermined direction. In the present embodiment, as illustrated in FIG. 4, the gate electrode 28 is formed with a part that extends from the gate line 29.

The gate insulating film 30 is formed on the substrate 20, and covers the gate electrode 28, as illustrated in FIG. 3. The gate insulating film 30 includes, for example, a silicon nitride film and a silicon oxide film. The silicon nitride film is formed in contact with the gate electrode 28 and the substrate 20. The silicon oxide film is formed in contact with the silicon nitride film. The silicon nitride film has a thickness of, for example, 100 to 400 nm. The silicon oxide film has a thickness of, for example, 50 to 100 nm. The gate insulating film 30 is formed by, for example, plasma CVD. In order to form a dense insulating film having a small gate leakage current at a low film forming temperature, a noble gas element such as argon or the like may be mixed in a reaction gas, so that the same is contained in the insulating film. The gate insulating film 30 may be composed of a silicon oxide film alone. In place of the silicon nitride film, an insulating film made of nitrided silicon oxide ($SiN_xO_y$) (x>y) may be formed. In place of the silicon oxide film, an insulating film made of oxidized silicon nitride ($SiO_xN_y$) (x>y) may be formed.

The semiconductor active layer 32 is formed in contact with the gate insulating film 30, as illustrated in FIG. 3. The semiconductor active layer 32 is formed with an oxide semiconductor. The oxide semiconductor is, for example, an oxide that contains indium (In), gallium (Ga), and zinc (Zn) at a predetermined ratio. The oxide semiconductor may be, for example, any one of $InGaO_3(ZnO)_5$, magnesium zinc oxide ($Mg_xZn_{1-x}O$), cadmium zinc oxide ($Cd_xZn_{1-x}O$), cadmium oxide (CdO), and In—Ga—Zn—O-type amorphous oxide semiconductor (a-IGZO). The oxide semiconductor may be, for example, amorphous ZnO, polycrystalline ZnO, or microcrystalline ZnO in which amorphous ZnO and polycrystalline ZnO are mixedly present, or alternatively, the foregoing ZnO to which an impurity element is added. The impurity element is, for example, one or a plurality of elements selected from the elements of the group I, the group XIII, the group XIV, the group XV, and the group XVII. The semiconductor active layer 32 has a thickness of, for example, 30 to 100 nm. The semiconductor active layer 32 is formed by, for example, forming a semiconductor layer by sputtering or the like, and patterning the semiconductor layer by photolithography. After the semiconductor layer is formed, or after the semiconductor active layer 32 is formed, a heat treatment may be carried out in an oxygen-containing atmosphere (for example, atmospheric air) at a high temperature (for example, at 350° C. or above). In this case, oxygen defects in the oxide semiconductor layer can be decreased.

As illustrated in FIG. 3, the source electrode 34 and the drain electrode 36 are formed in contact with the semiconductor active layer 32 and the gate insulating film 30. As illustrated in FIG. 4, the source electrode 34 is connected to the source line 35. The source electrode 34, the source line 35, and the drain electrode 36 are formed in the same layer. The source electrode 34, the source line 35, and the drain electrode 36 are, for example, made of a metal such as aluminum (Al), tungsten (W), molybdenum (Mo), tantalum (Ta), chromium (Cr), titanium (Ti), or copper (Cu), or an alloy of any of these, or alternatively, a nitride of any of the foregoing metals. The source electrode 34, the source line 35, and the drain electrode 36 may be, for example, a laminate of a plurality of metal films. In the present embodiment, the source electrode 34, the source line 35, and the drain electrode 36 have a laminate structure obtained by laminating a metal film made of titanium, a metal film made of aluminum, and a metal film made of titanium in the stated order. The source electrode 34, the source line 35, and the drain electrode 36 have a thickness of, for example, 50 to 500 nm. The source electrode 34, the source line 35, and the drain electrode 36 are formed by, for example, forming the metal films on the semiconductor active layer 32 and the gate insulating film 30 by sputtering or the like, and patterning the metal films by photolithography. The etching used when the metal films are patterned may be dry etching, or wet etching. In a case where a metal film formed on a large area substrate is etched, dry etching (anisotropic etching) is preferable, since it has a smaller line width shift, that is, a smaller line width variation.

As illustrated in FIG. 3, the image pickup panel 12 further includes an insulating film 38. The insulating film 38 covers the semiconductor active layer 32, the source electrode 34, the source line 35, and the drain electrode 36. The insulating film 38 functions as a passivation film. The insulating film 38 is, for example, a silicon oxide film. The insulating film 38 may be a silicon nitride film, or may be a laminate of a silicon nitride film and a silicon oxide film. The insulating film 38 has a thickness of, for example, 50 to 300 nm. The insulating film 38 is formed by, for example, plasma CVD.

After the insulating film 38 is formed, a heat treatment at a temperature of about 350° C. may be carried out. In this case, defects in the insulating film 38 can be decreased.

In the insulating film 38, a contact hole 381 is formed. The contact hole 381 overlaps the drain electrode 36 when viewed in a direction vertical to the principal surface of the substrate 20. The contact hole 381 is formed by, for example, photolithography.

As illustrated in FIG. 3, the photodiode 26 is connected via the contact hole 381 to the drain electrode 36. When viewed in the direction vertical to the principal surface of the substrate 20, an entirety of the photodiode 26 overlaps the drain electrode 36. The photodiode 26 includes an n-type amorphous silicon layer 26A, an intrinsic amorphous silicon layer 26B, and a p-type amorphous silicon layer 26C.

The n-type amorphous silicon layer 26A is made of amorphous silicon into which an n-type impurity (for example, phosphorus) is doped. The n-type amorphous silicon layer 26A is formed in contact with the electrode 36. The n-type amorphous silicon layer 26A has a thickness of, for example, 20 to 100 nm.

The intrinsic amorphous silicon layer 26B is made of intrinsic amorphous silicon. The intrinsic amorphous silicon layer 26B is formed in contact with the n-type amorphous silicon layer 26A. The intrinsic amorphous silicon layer 26B has a thickness of, for example, 200 to 2000 nm.

The p-type amorphous silicon layer 26C is made of amorphous silicon into which a p-type impurity (for example, boron) is doped. The p-type amorphous silicon layer 26C is formed in contact with the intrinsic amorphous silicon layer 26B. The p-type amorphous silicon layer 26C has a thickness of, for example, 10 to 50 nm.

The photodiode 26 is formed by, for example, forming a film made of n-type amorphous silicon, a film made of intrinsic amorphous silicon, and a film made of p-type amorphous silicon in the stated order by plasma CVD. Thereafter, these films are patterned by photolithography. As a result, the photodiode 26 is formed.

As illustrated in FIG. 3, the image pickup panel 12 further includes an electrode 40. The electrode 40 is formed in contact with, in the photodiode 22, the p-type amorphous silicon layer 26C. The electrode 40 covers an entirety of the p-type amorphous silicon layer 26C. The electrode 40 is, for example, a transparent conductive film. The transparent conductive film is made of, for example, indium zinc oxide. The electrode 40 is formed by, for example, forming a transparent conductive film by sputtering or the like, and thereafter, patterning the transparent conductive film by photolithography. The electrode 40 has a thickness of, for example, 50 to 500 nm.

As illustrated in FIG. 3, the image pickup panel 12 further includes a flattening film 44. The flattening film 44 is made of, for example, a photosensitive resin. The flattening film 44 covers the insulating film 42 and the electrode 40. The flattening film 44 has a thickness of, for example, 1000 to 4000 nm. The flattening film 44 is formed by, for example, applying the material by spin coating, slit coating, or the like, and thereafter carrying out a heat treatment in an atmosphere at 150 to 250° C. The temperature of the heat treatment for hardening the flattening film 44 is different depending on the material of the flattening film 44. In the flattening film 44, a contact hole 441 is formed. The contact hole 441 overlaps the electrode 40 when viewed in the direction vertical to the principal surface of the substrate 20. The contact hole 441 is formed by, for example, photolithography.

As illustrated in FIGS. 3 and 4, the image pickup panel 12 further includes a line 46. The line 46 is formed on the flattening film 44. As illustrated in FIG. 4, the line 46 extends in parallel to the source line 35. The line 46 overlaps the semiconductor active layer 32, when viewed in the direction vertical to the principal surface of the substrate 20. In the present embodiment, as illustrated in FIG. 4, the line 46 overlaps a part of the semiconductor active layer 32, the part being not in contact with the source electrode 34 and the drain electrode 36, when viewed in the direction vertical to the principal surface of the substrate 20. In the present embodiment, as illustrated in FIG. 4, when viewed in the direction vertical to the principal surface of the substrate 20, the line 46 overlaps a part of the semiconductor active layer 32, the part overlapping the gate electrode 28. As illustrated in FIG. 4, when viewed in the direction vertical to the principal surface of the substrate 20, the line 46 overlaps the electrode 40. The line 46 is made of, for example, a metal such as aluminum (Al), tungsten (W), molybdenum (Mo), tantalum (Ta), chromium (Cr), titanium (Ti), or copper (Cu), or an alloy of any of these, or alternatively, a nitride of the foregoing metal. The line 46 may be a transparent conductive film. The transparent conductive film is made of, for example, indium zinc oxide. The line 46 is in contact with the electrode 40 via the contact hole 441. The line 46 has a thickness of, for example, 50 to 500 nm. The line 46 is formed by, for example, forming a conductive film by sputtering or the like, and thereafter patterning the conductive film by photolithography.

As illustrated in FIGS. 3 and 4, the image pickup panel 12 further includes an electrode 52. The electrode 52 is formed in the same layer as the gate electrode 28. In other words, the electrode 52 is formed in contact with the principal surface of the substrate 20. The electrode 52 is made of the same material as that of the gate electrode 28. The electrode 52 is positioned below the drain electrode 36. The capacitor 50 is realized by the electrode 52, the drain electrode 36, and a portion of the insulating film 30 positioned between the electrodes 52, 36. The capacitor 50 accumulates charges. The electrode 52 is formed, for example, together with the gate electrode 28. The electrode 52 has the same thickness as that of the gate electrode 28.

As illustrated in FIG. 1, the control unit 14 includes a gate controller 14A, a signal reading part 14B, an image processor 14C, a bias controller 14D, an X-ray controller 14E, and a timing controller 14F. Though the control unit 14 is provided separately from the image pickup panel 12 in the example illustrated in FIG. 1, alternatively, a part of, or an entirety of the control unit 14 may be provided in the image pickup panel 12.

To the gate controller 14A, a plurality of gate lines 29 are connected, as illustrated in FIG. 2A. To each of the gate line 29, some of the pixel portions 22 are connected. In the example illustrated in FIG. 2A, four pixel portions 22 are connected to each gate line 29. The gate controller 14A selects one gate line 29 among the gate lines 29 based on the control signal from the timing controller 14F. The gate controller 14A applies a predetermined gate voltage through the selected gate line 29 to the thin film transistor 24 included in the pixel portion 22 connected to the gate line 29 (see FIG. 2B).

As illustrated in FIG. 2A, to the signal reading part 14B, a plurality of source lines 35 are connected. To each of the source lines 35, some of the pixel portions 22 are connected. In the example illustrated in FIG. 2A, four pixel portions 22 are connected to each source line 35. The signal reading part 14B selects one source line 35 out of the source lines 35 based on a control signal from the timing controller 14F. The signal reading part 14B reads out a light detection signal through the selected source line 35. Here, the light detection signal corresponds to charges accumulated in the capacitor 50. In other words, the magnitude of the light detection signal changes according to the amount of the charges accumulated in the capacitor 50. The pixel portion 22 from which the light detection signal is read out is connected to the source line 35 selected by the signal reading part 14B, and at the same time, connected to the gate line 29 selected by the gate controller 14A. The signal reading part 14B generates an image signal based on the light detection signal thus read out, and outputs the same to the image processor 14C.

The image processor 14C generates an image based on the image signal output from the signal reading part 14B.

The bias controller 14D is connected to the line 46. The bias controller 14D applies a predetermined voltage to the line 46 based on the control signal from the timing controller 14F. This causes a bias voltage to be applied to the photodiode 26.

The X-ray controller 14E controls the projection of X-ray by the X-ray source 16 based on the control signal from the timing controller 14F.

The timing controller 14F controls operation timings of the gate controller 14A, the signal reading part 14B, the bias controller 14D, and the and X-ray controller 14E.

Figure 5:
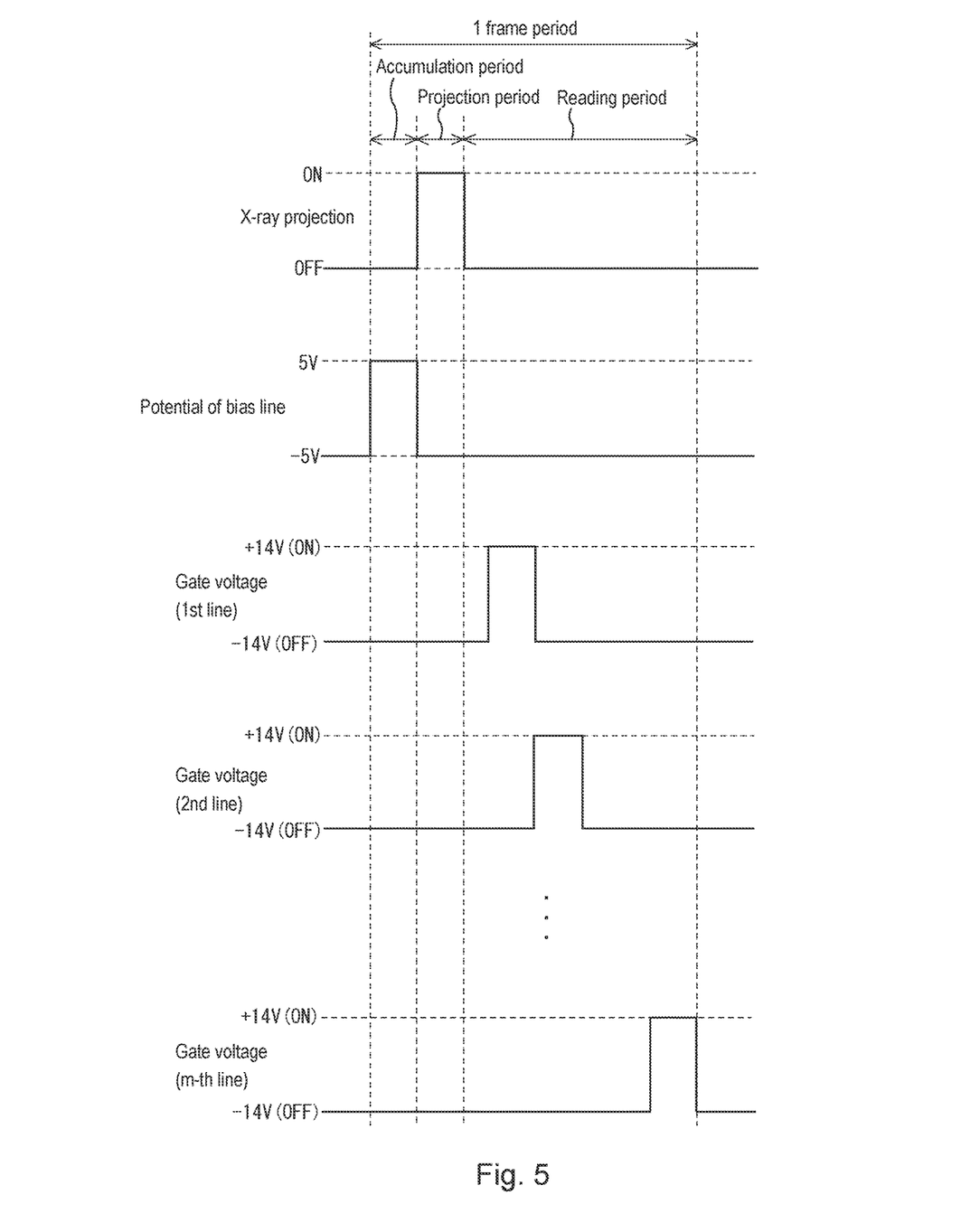
FIG. 5 is a timing chart illustrating the relationship between an X-ray projecting period in Embodiment 1, and respective potentials of gate electrodes.

The following describes operations of the X-ray image pickup system 10, while referring to FIG. 5.

First, the bias controller 14D applies a positive voltage to the line 46 over a predetermined period (accumulation period). This causes charges to be accumulated through the photodiode 26 in the capacitor 50.

After the predetermined period lapses, the bias controller 14D applies a negative voltage to the line 46. This causes a reverse bias voltage to be applied to the photodiode 26. As a result, a state in which charges are accumulated in the capacitor 50 is maintained.

At a timing at which the voltage applied to the line 46 is switched from a positive voltage to a negative voltage, the X-ray controller 14E causes the X-ray source 16 to operate, so as to project X-ray over a predetermined period (projection period). After the predetermined period lapses, the X-ray controller 14E causes the X-ray source 16 to operate, so as to end the projection of X-ray.

The projected X-ray is incident on the scintillator 13 through the object 18. The X-ray incident on the scintillator 13 is converted into scintillation light. The scintillation light is incident on the photodiode 26. Here, charges accumulated in the capacitor 50 flow out through the photodiode 26. In other words, in a case where scintillation light is detected by the photodiode 26, the amount of charges accumulated in the capacitor 50 decreases. To put it in another way, charges accumulated in the capacitor 50 correspond to the intensity of the scintillation light detected by the photodiode 26.

Thereafter, the light detection signal is read out by the gate controller 14A and the signal reading part 14B (reading period). In other words, charges accumulated in the capacitor 50 are read out. The signal reading part 14B generates an image signal based on the light detection signal thus read out. The image processor 14C generates an image based on the image signal thus generated.

Here, in the X-ray image pickup system 10, as illustrated in FIG. 5, the projection period while X-ray is projected, and the reading period while the light detection signal is read out, are provided individually. In other words, while X-ray is not projected, the light detection signal is read out. To put is in another way, X-ray is projected intermittently. This makes it possible to decrease the radiation exposure dose to the object 18.

The semiconductor active layer 32 of the thin film transistor 24 is made of an oxide semiconductor. This allows the off-current (leakage current) of the thin film transistor 24 to decrease. As a result, even if an image is generated based on charges accumulated in the capacitor 50, a target image can be obtained.

Embodiment 2

Figure 6:
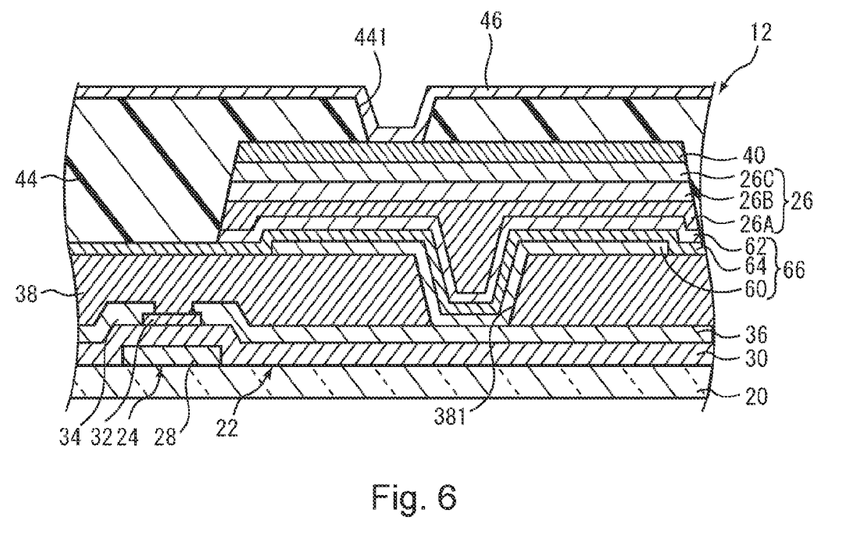
FIG. 6 is a cross-sectional view illustrating a schematic configuration of a pixel portion in Embodiment 2 of the present invention.
Figure 7:
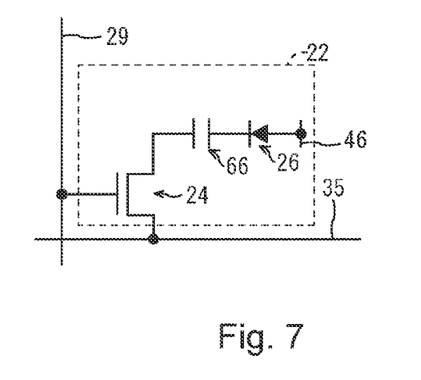
FIG. 7 illustrates an equivalent circuit of the pixel portion in Embodiment 2.

The following describes Embodiment 2 of the present invention, while referring to FIGS. 6 and 7. As illustrated in FIG. 6, no electrode 52 is formed in the present embodiment. In place of the electrode 52, an electrode 60, an electrode 62 and an insulating film 64 are formed.

The electrode 60 is formed in contact with the insulating film 38. The electrode 60 is in contact with the drain electrode 36 via the contact hole 381. The electrode 60 is made of, for example, a metal such as aluminum (Al), tungsten (W), molybdenum (Mo), tantalum (Ta), chromium (Cr), titanium (Ti), or copper (Cu), or an alloy of any of these, or alternatively, a nitride of the foregoing metal. The electrode 60 may be a transparent conductive film. The transparent conductive film is made of, for example, indium zinc oxide. The electrode 60 overlaps the photodiode 26 when viewed in the direction vertical to the principal surface of the substrate 20. The electrode 60 has a thickness of, for example, 50 to 200 nm. The electrode 60 is formed by, for example, forming a conductive film by sputtering or the like, and thereafter, patterning the conductive film by photolithography.

The insulating film 64 covers the insulating film 38 and the electrode 60. The insulating film 64 is, for example, a silicon nitride film. The insulating film 64 may be a silicon oxide film, or a laminate of a silicon nitride film and a silicon oxide film. The insulating film 64 has a thickness of, for example, 50 to 300 nm. The insulating film 64 is formed by, for example, plasma CVD. The flattening film 44 is formed in contact with the insulating film 64.

The electrode 62 is formed in contact with the insulating film 64. The n-type amorphous silicon layer 26A is formed in contact with the electrode 62. In other words, the photodiode 26 is formed in contact with the electrode 62. The electrode 62 is made of, for example, a metal such as aluminum (Al), tungsten (W), molybdenum (Mo), tantalum (Ta), chromium (Cr), titanium (Ti), or copper (Cu), or an alloy of any of these, or alternatively, a nitride of the foregoing metal. The electrode 62 may be a transparent conductive film. The transparent conductive film is made of, for example, indium zinc oxide. The electrode 62 overlaps the electrode 60 when viewed in the direction vertical to the principal surface of the substrate 20. The electrode 62 has a thickness of, for example, 50 to 200 nm. The electrode 62 is formed by, for example, forming a conductive film by sputtering or the like, and thereafter, patterning the conductive film by photolithography.

A capacitor 66 is formed with the electrode 60, the electrode 62, and a portion of the insulating film 64 that is positioned between the electrodes 60, 62. As illustrated in FIG. 7, the capacitor 66 is connected in series with respect to the photodiode 26. The capacitor 66 is connected to the drain electrode 36.

In the X-ray image pickup system of the present embodiment, the timings of start and end of the projection of X-ray, the timings of start and end of the application of the bias voltage, and the timings of start and end of the reading of the light detection signal are identical to those in Embodiment 1. The following describes operations of the X-ray image pickup system of the present embodiment, while referring to FIG. 5.

First of all, the bias controller 14D applies a positive voltage to the line 46 over a predetermined period (accumulation period). This causes charges to be accumulated in the capacitor 66 through the photodiode 26.

After the predetermined period lapses, the bias controller 14D applies a negative voltage to the line 46. This causes a reverse bias voltage to be applied to the photodiode 26. As a result, a state in which charges are accumulated in the capacitor 66 is maintained.

At a timing when the voltage to be applied to the line 46 is switched from a positive voltage to a negative voltage, the X-ray controller 14E causes the X-ray source 16 to operate, so as to project X-ray over a predetermined period (projection period). After the predetermined period lapses, the X-ray controller 14E causes the X-ray source 16 to operate, so as to end the projection of X-ray.

The projected X-ray is incident on the scintillator 13 through the object 18. The X-ray incident on the scintillator 13 is converted into scintillation light. The scintillation light is incident on the photodiode 26. Here, charges accumulated in the capacitor 66 flow out through the photodiode 26. In other words, in a case where scintillation light is detected by the photodiode 26, the amount of charges accumulated in the capacitor 66 decreases. To put it in another way, charges accumulated in the capacitor 66 correspond to the intensity of the scintillation light detected by the photodiode 26.

Thereafter, the light detection signal is read out by the gate controller 14A and the signal reading part 14B. In other words, charges accumulated in the capacitor 66 are read out. The signal reading part 14B generates an image signal based on the light detection signal thus read out. The image processor 14C generates an image based on the image signal thus generated.

In the present embodiment as well, effects identical to those in Embodiment 1 can be achieved.

In the present embodiment, the capacitor 66 is connected in series with respect to the photodiode 26. When charges accumulated in the capacitor 66 are read out, therefore, leakage of the charges due to the photodiode 26 can be prevented. This makes it possible to improve the quality of an image generated based on charges read out.

The embodiments of the present invention, described above in detail, are merely examples, and the present invention is not limited by the above-described embodiments at all.

The invention claimed is:

1. An X-ray image pickup system comprising:
an X-ray source;
an image pickup panel;
a scintillator that is arranged between the X-ray source and the image pickup panel, and that converts X-rays projected from the X-ray source into scintillation light; and
X-ray control circuitry that controls an operation of the X-ray source, wherein
the image pickup panel includes:
a photoelectric conversion element to which the scintillation light is projected;
a capacitor that is connected to the photoelectric conversion element and accumulates charges;
a thin film transistor that is connected to the capacitor; and
TFT control circuitry that controls an operation of the thin film transistor,
the thin film transistor includes a semiconductor active layer made of an oxide semiconductor,
the X-ray control circuitry causes the X-ray source to project the X-rays intermittently,
the TFT control circuitry causes the thin film transistor to operate when the X-rays are not projected, so as to read out the charges accumulated in the capacitor,
the thin film transistor includes a drain electrode connected to the capacitor, and
the photoelectric conversion element is connected in series with the capacitor.

2. The X-ray image pickup system according to claim 1, wherein the thin film transistor includes:
a gate electrode;
a first insulating film that is formed between the gate electrode and the semiconductor active layer and covers the gate electrode; and
a second insulating film that covers the semiconductor active layer, wherein each of the first insulating film and the second insulating film includes a silicon oxide film formed in contact with the semiconductor active layer.

3. The X-ray image pickup system according to claim 1, wherein the oxide semiconductor is an oxide that contains indium (In), gallium (Ga), and zinc (Zn) at a predetermined ratio.

4. The X-ray image pickup system according to claim 1, wherein the drain electrode is directly electrically connected to the capacitor in series.

* * * * *